(12) United States Patent
Cheng et al.

(10) Patent No.: US 12,385,918 B2
(45) Date of Patent: Aug. 12, 2025

(54) IgA ANTIBODIES AND KITS CAPABLE OF SPECIFICALLY RECOGNIZING RBD PROTEIN

(71) Applicant: SHENZHEN YHLO BIOTECH CO., LTD, Shenzhen (CN)

(72) Inventors: Fangming Cheng, Shenzhen (CN); Xiaotao Lin, Shenzhen (CN); Zhisheng Dang, Shenzhen (CN); Liqiang Wu, Shenzhen (CN); Chungen Qian, Shenzhen (CN); Kunhui Hu, Shenzhen (CN)

(73) Assignee: SHENZHEN YHLO BIOTECH CO., LTD, Shenzhen (CN)

( * ) Notice: Subject to any disclaimer, the term of this patent is extended or adjusted under 35 U.S.C. 154(b) by 585 days.

(21) Appl. No.: 17/776,182

(22) PCT Filed: Nov. 20, 2020

(86) PCT No.: PCT/CN2020/130496
§ 371 (c)(1),
(2) Date: May 11, 2022

(87) PCT Pub. No.: WO2022/007304
PCT Pub. Date: Jan. 13, 2022

(65) Prior Publication Data
US 2023/0220052 A1   Jul. 13, 2023

(30) Foreign Application Priority Data
Jul. 6, 2020 (CN) .......................... 202010639269.X (51) Int. Cl.
*C07K 16/08* (2006.01)
*C07K 16/10* (2006.01)
*G01N 33/543* (2006.01)
*G01N 33/569* (2006.01)

(52) U.S. Cl.
CPC ... *G01N 33/56983* (2013.01); *C07K 16/1003* (2023.08); *G01N 33/54326* (2013.01); *C07K 2317/24* (2013.01); *C07K 2317/52* (2013.01); *C07K 2317/565* (2013.01); *C07K 2317/92* (2013.01); *G01N 2333/165* (2013.01); *G01N 2469/20* (2013.01)

(58) Field of Classification Search
CPC ....... G01N 33/56983; G01N 33/54326; G01N 2333/165; G01N 2469/20; G01N 33/6854; G01N 2469/10; C07K 16/1003; C07K 2317/24; C07K 2317/52; C07K 2317/565; C07K 2317/92; C07K 16/10
See application file for complete search history.

(56) References Cited

FOREIGN PATENT DOCUMENTS

| CN | 111187354 A | 5/2020 |
| CN | 111239392 A | 6/2020 |
| CN | 111285933 A | 6/2020 |
| CN | 111303254 A | 6/2020 |
| CN | 111303279 A | 6/2020 |
| CN | 111303280 A | 6/2020 |
| CN | 111366735 A | 7/2020 |
| CN | 111690060 A | 9/2020 |

OTHER PUBLICATIONS

Ma, H., Zeng, W., He, H et al. COVID-19 diagnosis and study of serum SARS-CoV-2 specific IgA, IgM and IgG by chemiluminescence immunoanalysis. medRxiv Apr. 17, 2020. https://doi.org/10.1101/2020.04.17.20064907 (Year: 2020).*
International Search Report and Written Opinion, and English Translation thereof, for International Application No. PCT/CN2020/130496, mailed Apr. 9, 2021, (15 pages).
Chinese Office Action for Chinese Application No. 202010639269.X mailed Oct. 21, 2021, (15 pages).
Tai, W., et al. (2020) "Identification of SARS-CoV RBD-targeting monoclonal antibodies with crossreactive or neutralizing activity against SARS-CoV-2," Antiviral Research, 179:104820 (6 pages).
Lan, J., et al. (2020) "Structure of the SARS-CoV-2 spike receptor-binding domain bound to the ACE2 receptor," Nature, 581:215-220 (16 pages).
Ma, H., et al. (2020) "Serum IgA, IgM, and IgG responses in COVID-19," Cellular & Molecular Immunology, 17:773-775 5 (3 pages).
Extended European Search Report for European Counterpart Application No. 20944585.7, mailed Jun. 27, 2024, (7 pages).
Ejemel, M., et al. (2020) "IgA MAb blocks SARS-CoV-2 Spike-ACE2 interaction providing mucosal immunity," BioRxiv. May 2020.

* cited by examiner

*Primary Examiner* — Bao-Thuy L Nguyen
*Assistant Examiner* — Christopher Evans
(74) *Attorney, Agent, or Firm* — Kagan Binder, PLLC (57) ABSTRACT

The disclosure relates to the technical field of virus detection, in particular, to an IgA antibody and a kit capable of specifically recognizing RBD protein. The antibody can be used as a calibrator of IgA antibody against the RBD protein of SARS-CoV-2. the disclosure further relates to a kit comprising the antibody which enables automated, high-throughput, and rapid detection of IgA antibody against novel coronavirus pneumonia.

17 Claims, 1 Drawing Sheet
Specification includes a Sequence Listing.

SEQUENCE LISTING

```
<160> NUMBER OF SEQ ID NOS: 20

<210> SEQ ID NO 1
<211> LENGTH: 24
<212> TYPE: PRT
<213> ORGANISM: artificial sequence
<220> FEATURE:
<223> OTHER INFORMATION: heavy chain complementarity determining region
      H-CDR1

<400> SEQUENCE: 1

Gly Gly Cys Thr Ala Cys Gly Gly Cys Thr Thr Cys Ala Thr Cys Ala
1               5                   10                  15

Cys Ala Thr Ala Cys Thr Gly Gly
            20

<210> SEQ ID NO 2
<211> LENGTH: 24
<212> TYPE: PRT
<213> ORGANISM: artificial sequence
<220> FEATURE:
<223> OTHER INFORMATION: heavy chain complementarity determining region
      H-CDR2

<400> SEQUENCE: 2

Ala Thr Cys Thr Ala Cys Cys Cys Gly Gly Cys Gly Ala Cys Ala
1               5                   10                  15

Gly Cys Gly Ala Gly Ala Cys Cys
            20

<210> SEQ ID NO 3
<211> LENGTH: 36
<212> TYPE: PRT
<213> ORGANISM: artificial sequence
<220> FEATURE:
<223> OTHER INFORMATION: heavy chain complementarity determining region
      H-CDR3

<400> SEQUENCE: 3

Gly Cys Cys Gly Gly Cys Gly Gly Cys Thr Cys Cys Gly Gly Cys Ala
1               5                   10                  15

Thr Cys Ala Gly Cys Ala Cys Cys Cys Thr Ala Thr Gly Gly Ala
            20                  25                  30

Thr Gly Thr Gly
        35
```

-continued

<210> SEQ ID NO 4
<211> LENGTH: 36
<212> TYPE: PRT
<213> ORGANISM: artificial sequence
<220> FEATURE:
<223> OTHER INFORMATION: light chain complementarity determining region L-CDR1

<400> SEQUENCE: 4

```
Cys Ala Gly Thr Cys Cys Gly Thr Gly Cys Thr Gly Thr Ala Cys Ala
1               5                   10                  15

Gly Cys Thr Cys Cys Ala Thr Cys Ala Ala Thr Ala Ala Gly Ala Ala
            20                  25                  30

Thr Thr Ala Cys
        35
```

<210> SEQ ID NO 5
<211> LENGTH: 9
<212> TYPE: PRT
<213> ORGANISM: artificial sequence
<220> FEATURE:
<223> OTHER INFORMATION: light chain complementarity determining region L-CDR2

<400> SEQUENCE: 5

```
Thr Gly Gly Gly Cys Cys Ala Gly Cys
1               5
```

<210> SEQ ID NO 6
<211> LENGTH: 27
<212> TYPE: PRT
<213> ORGANISM: artificial sequence
<220> FEATURE:
<223> OTHER INFORMATION: light chain complementarity determining region L-CDR3

<400> SEQUENCE: 6

```
Cys Ala Gly Cys Ala Gly Thr Ala Cys Thr Ala Cys Thr Cys Cys Ala
1               5                   10                  15

Cys Ala Cys Cys Cys Thr Ala Cys Ala Cys Ala
            20                  25
```

<210> SEQ ID NO 7
<211> LENGTH: 132
<212> TYPE: PRT
<213> ORGANISM: artificial sequence
<220> FEATURE:
<223> OTHER INFORMATION: heavy chain framework region H-FR1

<400> SEQUENCE: 7

```
Ala Thr Gly Gly Cys Cys Cys Cys Ala Gly Cys Cys Cys Ala Gly Thr
1               5                   10                  15

Thr Thr Cys Thr Gly Gly Gly Cys Cys Thr Gly Cys Thr Gly Cys Thr
            20                  25                  30

Gly Cys Thr Gly Thr Gly Thr Thr Thr Cys Cys Ala Gly Gly Gly Cys
        35                  40                  45

Ala Cys Ala Ala Gly Gly Thr Gly Cys Cys Ala Gly Ala Thr Gly Cys
    50                  55                  60

Ala Gly Cys Thr Gly Gly Thr Gly Cys Ala Gly Thr Cys Cys Gly Gly
65                  70                  75                  80

Cys Ala Cys Ala Gly Ala Gly Gly Thr Gly Ala Ala Gly Ala Ala Gly
                85                  90                  95
```

Cys Cys Thr Gly Gly Cys Gly Ala Gly Ala Gly Cys Cys Thr Gly Ala
            100                 105                 110

Ala Gly Ala Thr Cys Ala Gly Cys Thr Gly Thr Ala Ala Gly Gly Gly
        115                 120                 125

Cys Thr Cys Cys
    130

<210> SEQ ID NO 8
<211> LENGTH: 51
<212> TYPE: PRT
<213> ORGANISM: artificial sequence
<220> FEATURE:
<223> OTHER INFORMATION: heavy chain framework region H-FR2

<400> SEQUENCE: 8

Ala Thr Cys Gly Gly Cys Thr Gly Gly Thr Gly Ala Gly Gly Cys
1               5                   10                  15

Ala Gly Ala Thr Gly Cys Cys Cys Gly Gly Cys Ala Ala Gly Gly Gly
            20                  25                  30

Cys Cys Thr Gly Gly Ala Gly Thr Gly Gly Ala Thr Gly Gly Gly Cys
        35                  40                  45

Ala Thr Cys
    50

<210> SEQ ID NO 9
<211> LENGTH: 114
<212> TYPE: PRT
<213> ORGANISM: artificial sequence
<220> FEATURE:
<223> OTHER INFORMATION: heavy chain framework region H-FR3

<400> SEQUENCE: 9

Ala Gly Gly Thr Ala Cys Ala Gly Cys Cys Thr Ala Gly Cys Thr
1               5                   10                  15

Thr Thr Cys Ala Gly Gly Gly Cys Cys Ala Gly Gly Thr Gly Ala Cys
            20                  25                  30

Cys Ala Thr Cys Ala Gly Cys Gly Cys Cys Gly Ala Cys Ala Ala Gly
        35                  40                  45

Ala Gly Cys Ala Thr Cys Ala Ala Cys Ala Gly Cys Cys Thr
    50                  55                  60

Ala Cys Cys Thr Gly Cys Ala Gly Thr Gly Gly Ala Gly Cys Ala Gly
65                  70                  75                  80

Cys Cys Thr Gly Ala Ala Gly Cys Cys Thr Cys Cys Gly Ala Cys Ala
            85                  90                  95

Ala Cys Ala Gly Cys Cys Ala Thr Cys Thr Ala Cys Thr Ala Cys Thr
                100                 105                 110

Gly Cys

<210> SEQ ID NO 10
<211> LENGTH: 27
<212> TYPE: PRT
<213> ORGANISM: artificial sequence
<220> FEATURE:
<223> OTHER INFORMATION: heavy chain framework region H-FR4

<400> SEQUENCE: 10

Thr Gly Gly Gly Gly Cys Cys Ala Gly Gly Cys Ala Cys Ala Ala
1               5                   10                  15

Cys Ala Gly Thr Gly Ala Cys Cys Gly Thr Gly
            20                  25

<210> SEQ ID NO 11
<211> LENGTH: 135
<212> TYPE: PRT
<213> ORGANISM: artificial sequence
<220> FEATURE:
<223> OTHER INFORMATION: light chain framework region L-FR1

<400> SEQUENCE: 11

Ala Thr Gly Gly Cys Cys Cys Ala Gly Cys Cys Ala Gly Thr
1               5                   10                  15

Thr Cys Cys Thr Gly Gly Gly Cys Cys Thr Gly Cys Thr Gly Cys Thr
            20                  25                  30

Gly Cys Thr Gly Thr Gly Cys Thr Thr Thr Cys Ala Gly Gly Gly Cys
        35                  40                  45

Ala Cys Ala Ala Gly Ala Thr Gly Cys Gly Ala Thr Ala Thr Cys Cys
50                  55                  60

Ala Gly Cys Thr Gly Ala Cys Cys Cys Ala Gly Thr Cys Cys Cys
65                  70                  75                  80

Cys Gly Ala Cys Thr Cys Cys Thr Gly Gly Cys Cys Gly Thr Gly
            85                  90                  95

Thr Cys Cys Cys Thr Gly Gly Ala Gly Ala Gly Ala Gly Ala Gly
                100                 105                 110

Cys Cys Ala Cys Ala Ala Thr Cys Ala Ala Cys Thr Gly Thr Ala Ala
            115                 120                 125

Gly Ala Gly Cys Thr Cys Cys
        130                 135

<210> SEQ ID NO 12
<211> LENGTH: 51
<212> TYPE: PRT
<213> ORGANISM: artificial sequence
<220> FEATURE:
<223> OTHER INFORMATION: light chain framework region L-FR2

<400> SEQUENCE: 12

Cys Thr Gly Gly Cys Cys Thr Gly Gly Thr Ala Cys Cys Ala Gly Cys
1               5                   10                  15

Ala Gly Ala Ala Gly Cys Cys Thr Gly Gly Cys Ala Gly Cys Cys
            20                  25                  30

Thr Cys Cys Cys Ala Ala Gly Cys Thr Gly Cys Thr Gly Ala Thr Cys
        35                  40                  45

Thr Ala Cys
    50

<210> SEQ ID NO 13
<211> LENGTH: 108
<212> TYPE: PRT
<213> ORGANISM: artificial sequence
<220> FEATURE:
<223> OTHER INFORMATION: light chain framework region L-FR3

<400> SEQUENCE: 13

Ala Cys Cys Ala Gly Ala Gly Ala Gly Thr Cys Cys Gly Gly Cys Gly
1               5                   10                  15

Thr Gly Cys Cys Cys Gly Ala Thr Ala Gly Gly Thr Thr Cys Ala Gly
            20                  25                  30

Cys Gly Gly Cys Ala Gly Cys Gly Gly Cys Ala Gly Cys Gly Gly Ala
        35                  40                  45

```
Ala Cys Ala Gly Ala Thr Thr Thr Cys Ala Cys Cys Thr Gly Ala
        50                  55                  60
Cys Cys Ala Thr Cys Ala Gly Cys Ala Gly Cys Cys Thr Gly Cys Ala
65                  70                  75                  80
Gly Gly Cys Cys Gly Ala Gly Ala Thr Gly Thr Gly Gly Cys Cys
                85                  90                  95
Gly Thr Gly Thr Ala Cys Thr Ala Cys Thr Gly Cys
            100                 105
```

<210> SEQ ID NO 14
<211> LENGTH: 30
<212> TYPE: PRT
<213> ORGANISM: artificial sequence
<220> FEATURE:
<223> OTHER INFORMATION: light chain framework region L-FR4

<400> SEQUENCE: 14

```
Thr Thr Cys Gly Gly Cys Cys Ala Gly Gly Gly Cys Ala Cys Cys Ala
1               5                   10                  15
Ala Gly Gly Thr Gly Gly Ala Gly Ala Thr Cys Ala Ala Gly
                20                  25                  30
```

<210> SEQ ID NO 15
<211> LENGTH: 201
<212> TYPE: PRT
<213> ORGANISM: artificial sequence
<220> FEATURE:
<223> OTHER INFORMATION: the RBD protein of the recombinant RBD protein

<400> SEQUENCE: 15

```
Asn Ile Thr Asn Leu Cys Pro Phe Gly Glu Val Phe Asn Ala Thr Arg
1               5                   10                  15
Phe Ala Ser Val Tyr Ala Trp Asn Arg Lys Arg Ile Ser Asn Cys Val
                20                  25                  30
Ala Asp Tyr Ser Val Leu Tyr Asn Ser Ala Ser Phe Ser Thr Phe Lys
            35                  40                  45
Cys Tyr Gly Val Ser Pro Thr Lys Leu Asn Asp Leu Cys Phe Thr Asn
50                  55                  60
Val Tyr Ala Asp Ser Phe Val Ile Arg Gly Asp Glu Val Arg Gln Ile
65                  70                  75                  80
Ala Pro Gly Gln Thr Gly Lys Ile Ala Asp Tyr Asn Tyr Lys Leu Pro
                85                  90                  95
Asp Asp Phe Thr Gly Cys Val Ile Ala Trp Asn Ser Asn Asn Leu Asp
            100                 105                 110
Ser Lys Val Gly Gly Asn Tyr Asn Tyr Leu Tyr Arg Leu Phe Arg Lys
        115                 120                 125
Ser Asn Leu Lys Pro Phe Glu Arg Asp Ile Ser Thr Glu Ile Tyr Gln
    130                 135                 140
Ala Gly Ser Thr Pro Cys Asn Gly Val Glu Gly Phe Asn Cys Tyr Phe
145                 150                 155                 160
Pro Leu Gln Ser Tyr Gly Phe Gln Pro Thr Asn Gly Val Gly Tyr Gln
                165                 170                 175
Pro Tyr Arg Val Val Val Leu Ser Phe Glu Leu Leu His Ala Pro Ala
            180                 185                 190
Thr Val Cys Gly Pro Lys Lys Ser Thr
        195                 200
```

<210> SEQ ID NO 16

```
<211> LENGTH: 23
<212> TYPE: PRT
<213> ORGANISM: artificial sequence
<220> FEATURE:
<223> OTHER INFORMATION: the transmembrane domain of the recombinant RBD
      protein

<400> SEQUENCE: 16

Glu Leu Trp Leu Val Leu Val Ala Val Gly Ala Gly Leu Leu Leu Leu
1               5                   10                  15

Gly Leu Ile Ile Leu Leu Leu
            20

<210> SEQ ID NO 17
<211> LENGTH: 16
<212> TYPE: PRT
<213> ORGANISM: artificial sequence
<220> FEATURE:
<223> OTHER INFORMATION: the tag sequence of the recombinant RBD protein

<400> SEQUENCE: 17

Trp Gly Gln Gly Gly Thr His Gly Gln Trp Asn Lys Pro Ser Lys Pro
1               5                   10                  15

<210> SEQ ID NO 18
<211> LENGTH: 16
<212> TYPE: PRT
<213> ORGANISM: artificial sequence
<220> FEATURE:
<223> OTHER INFORMATION: the signal peptide of the recombinant RBD
      protein

<400> SEQUENCE: 18

Met Phe Val Phe Leu Val Leu Leu Pro Leu Val Ser Ser Gln Cys Val
1               5                   10                  15

<210> SEQ ID NO 19
<211> LENGTH: 1074
<212> TYPE: PRT
<213> ORGANISM: Homo sapiens
<220> FEATURE:
<223> OTHER INFORMATION: the constant region of the heavy chain of the
      recombinant RBD protein

<400> SEQUENCE: 19

Ala Gly Cys Thr Cys Cys Gly Cys Thr Ala Cys Gly Cys Ala Thr
1               5                   10                  15

Cys Cys Cys Cys Gly Ala Cys Cys Ala Gly Cys Cys Cys Ala Ala
                20                  25                  30

Gly Gly Thr Cys Thr Thr Cys Cys Cys Gly Cys Thr Gly Ala Gly Cys
            35                  40                  45

Cys Thr Cys Thr Gly Cys Ala Gly Cys Ala Cys Cys Cys Ala Gly Cys
        50                  55                  60

Cys Ala Gly Ala Thr Gly Gly Gly Ala Ala Cys Gly Thr Gly Gly Thr
65                  70                  75                  80

Cys Ala Thr Cys Gly Cys Cys Thr Gly Cys Cys Thr Gly Gly Thr Cys
                85                  90                  95

Cys Ala Gly Gly Gly Cys Thr Thr Cys Thr Thr Cys Cys Cys Cys
                100                 105                 110

Ala Gly Gly Ala Gly Cys Cys Ala Cys Thr Cys Ala Gly Thr Gly Thr
            115                 120                 125

Gly Ala Cys Cys Thr Gly Gly Ala Gly Cys Gly Ala Ala Ala Gly Cys
            130                 135                 140
```

```
Gly Gly Ala Cys Ala Gly Gly Cys Gly Thr Gly Ala Cys Cys Gly
145                 150                 155                 160

Cys Cys Ala Gly Ala Ala Ala Cys Thr Thr Cys Cys Ala Cys Cys
                165                 170                 175

Cys Ala Gly Cys Cys Ala Gly Gly Ala Thr Gly Cys Cys Thr Cys Cys
            180                 185                 190

Gly Gly Gly Gly Ala Cys Cys Thr Gly Thr Ala Cys Ala Cys Cys Ala
                195                 200                 205

Cys Gly Ala Gly Cys Ala Gly Cys Cys Ala Gly Cys Thr Gly Ala Cys
        210                 215                 220

Cys Cys Thr Gly Cys Cys Gly Gly Cys Cys Ala Cys Ala Cys Ala Gly
225                 230                 235                 240

Thr Gly Cys Cys Thr Ala Gly Cys Cys Gly Gly Cys Ala Ala Gly Thr
            245                 250                 255

Cys Cys Gly Thr Gly Ala Cys Ala Thr Gly Cys Cys Ala Cys Gly Thr
            260                 265                 270

Gly Ala Ala Gly Cys Ala Cys Thr Ala Cys Ala Cys Gly Ala Ala Thr
        275                 280                 285

Cys Cys Cys Ala Gly Cys Cys Ala Gly Gly Ala Thr Gly Thr Gly Ala
290                 295                 300

Cys Thr Gly Thr Gly Cys Cys Cys Thr Gly Cys Cys Cys Ala Gly Thr
305                 310                 315                 320

Thr Cys Cys Cys Thr Cys Ala Ala Cys Thr Cys Cys Ala Cys Cys Thr
            325                 330                 335

Ala Cys Cys Cys Cys Ala Thr Cys Thr Cys Cys Cys Thr Cys Ala Ala
            340                 345                 350

Cys Thr Cys Cys Ala Cys Cys Thr Ala Cys Cys Cys Cys Ala Thr Cys
        355                 360                 365

Thr Cys Cys Cys Thr Cys Ala Thr Gly Cys Thr Gly Cys Cys Ala Cys
    370                 375                 380

Cys Cys Cys Cys Gly Ala Cys Thr Gly Thr Cys Ala Cys Thr Gly Cys
385                 390                 395                 400

Ala Cys Cys Gly Ala Cys Cys Gly Gly Cys Cys Cys Thr Cys Gly Ala
                405                 410                 415

Gly Gly Ala Cys Cys Thr Gly Cys Thr Cys Thr Thr Ala Gly Gly Thr
            420                 425                 430

Thr Cys Ala Gly Ala Ala Gly Cys Gly Ala Ala Cys Cys Thr Cys Ala
        435                 440                 445

Cys Gly Thr Gly Cys Ala Cys Ala Cys Thr Gly Ala Cys Cys Gly Gly
    450                 455                 460

Cys Cys Thr Gly Ala Gly Ala Gly Ala Thr Gly Cys Cys Thr Cys Ala
465                 470                 475                 480

Gly Gly Thr Gly Thr Cys Ala Cys Cys Thr Thr Cys Ala Cys Cys Thr
                485                 490                 495

Gly Gly Ala Cys Gly Cys Cys Cys Thr Cys Ala Ala Gly Thr Gly Gly
            500                 505                 510

Gly Ala Ala Gly Ala Gly Cys Gly Cys Thr Gly Thr Thr Cys Ala Ala
        515                 520                 525

Gly Gly Ala Cys Cys Ala Cys Cys Thr Gly Ala Gly Cys Gly Thr Gly
    530                 535                 540

Ala Cys Cys Thr Cys Thr Gly Thr Gly Gly Cys Thr Gly Cys Thr Ala
545                 550                 555                 560
```

-continued

```
Cys Ala Gly Cys Gly Thr Gly Thr Cys Cys Ala Thr Gly Thr Cys
                565                 570                 575
Cys Thr Gly Cys Cys Gly Gly Cys Thr Gly Thr Cys Cys Gly
        580                 585                 590
Ala Gly Cys Cys Ala Thr Gly Ala Ala Cys Cys Ala Thr Gly Gly
        595                 600                 605
Gly Ala Ala Gly Ala Cys Cys Thr Thr Cys Ala Cys Thr Thr Gly Cys
        610                 615                 620
Ala Cys Thr Gly Cys Thr Gly Cys Cys Thr Ala Cys Cys Cys Gly
625                 630                 635                 640
Ala Gly Thr Cys Cys Ala Ala Gly Ala Cys Cys Cys Gly Cys Thr
                645                 650                 655
Ala Ala Cys Cys Gly Cys Cys Ala Cys Cys Thr Cys Thr Cys Ala
                660                 665                 670
Ala Ala Ala Thr Cys Cys Gly Gly Ala Ala Ala Cys Ala Cys Ala Thr
        675                 680                 685
Thr Cys Gly Gly Cys Cys Cys Gly Ala Gly Gly Thr Cys Cys Ala
        690                 695                 700
Cys Cys Thr Gly Cys Thr Gly Cys Cys Gly Cys Cys Gly Cys Cys Gly
705                 710                 715                 720
Thr Cys Gly Gly Ala Gly Gly Ala Gly Cys Thr Gly Cys Cys Cys
                725                 730                 735
Thr Gly Ala Ala Cys Gly Ala Gly Cys Thr Gly Gly Thr Gly Ala Cys
                740                 745                 750
Gly Cys Thr Gly Ala Cys Gly Thr Gly Cys Cys Thr Gly Gly Cys Ala
                755                 760                 765
Cys Gly Thr Gly Cys Thr Thr Cys Ala Gly Cys Cys Cys Cys Ala
                770                 775                 780
Ala Gly Gly Ala Thr Gly Thr Gly Cys Thr Gly Thr Thr Cys Gly
785                 790                 795                 800
Cys Thr Gly Gly Cys Thr Gly Cys Ala Gly Gly Gly Thr Cys Ala
                805                 810                 815
Cys Ala Gly Gly Ala Gly Cys Thr Gly Cys Cys Cys Cys Gly Cys Gly
                820                 825                 830
Ala Gly Ala Ala Gly Thr Ala Cys Cys Thr Gly Ala Cys Thr Thr Gly
        835                 840                 845
Gly Gly Cys Ala Thr Cys Cys Cys Gly Gly Cys Ala Gly Gly Ala Gly
        850                 855                 860
Cys Cys Cys Ala Gly Cys Cys Ala Gly Gly Cys Ala Cys Cys Ala
865                 870                 875                 880
Cys Cys Ala Cys Cys Thr Thr Cys Gly Cys Thr Gly Thr Gly Ala Cys
                885                 890                 895
Cys Ala Gly Cys Ala Thr Ala Cys Thr Gly Cys Gly Cys Gly Thr Gly
        900                 905                 910
Gly Cys Ala Gly Cys Cys Gly Ala Gly Ala Cys Thr Gly Gly Ala
        915                 920                 925
Ala Gly Ala Ala Gly Gly Gly Gly Ala Cys Ala Cys Cys Thr Thr
        930                 935                 940
Cys Thr Cys Cys Thr Gly Cys Ala Thr Gly Gly Thr Gly Gly Gly Cys
945                 950                 955                 960
Cys Ala Cys Gly Ala Gly Gly Cys Cys Cys Thr Gly Cys Cys Gly Cys
        965                 970                 975
Thr Gly Gly Cys Cys Thr Thr Cys Ala Cys Ala Cys Ala Gly Ala Ala
```

```
                980             985             990
Gly Ala Cys Cys Ala Thr Cys Gly Ala Cys Cys Gly Cys Thr Thr Gly
            995             1000            1005
Gly Cys Gly Gly Gly Thr Ala Ala Ala Cys Cys Ala Cys Cys
    1010            1015            1020
Cys Ala Thr Gly Thr Cys Ala Ala Thr Gly Thr Gly Thr Cys Thr
    1025            1030            1035
Gly Thr Thr Gly Thr Cys Ala Thr Gly Gly Cys Gly Gly Ala Gly
    1040            1045            1050
Gly Thr Gly Gly Ala Cys Gly Gly Cys Ala Cys Cys Thr Gly Cys
    1055            1060            1065
Thr Ala Cys Thr Gly Ala
    1070
```

<210> SEQ ID NO 20
<211> LENGTH: 318
<212> TYPE: PRT
<213> ORGANISM: Homo sapiens
<220> FEATURE:
<223> OTHER INFORMATION: the constant region of the light chain of the
      recombinant RBD protein

<400> SEQUENCE: 20

```
Gly Thr Gly Gly Cys Thr Gly Cys Ala Cys Cys Ala Thr Cys Thr Gly
1               5                   10                  15
Thr Cys Thr Thr Cys Ala Thr Cys Thr Thr Cys Cys Gly Cys Cys
                20                  25                  30
Ala Thr Cys Thr Gly Ala Thr Gly Ala Gly Cys Ala Gly Thr Thr Gly
                35                  40                  45
Ala Ala Ala Thr Cys Thr Gly Gly Ala Ala Cys Thr Gly Cys Cys Thr
    50                  55                      60
Cys Thr Gly Thr Thr Gly Thr Gly Thr Gly Cys Cys Thr Gly Cys Thr
65                  70                      75                  80
Gly Ala Ala Thr Ala Ala Cys Thr Thr Cys Thr Ala Thr Cys Cys Cys
                85                  90                  95
Ala Gly Ala Gly Ala Gly Gly Cys Cys Ala Ala Ala Gly Thr Ala Cys
                100                 105                 110
Ala Gly Thr Gly Gly Ala Ala Gly Gly Thr Gly Gly Ala Thr Ala Ala
                115                 120                 125
Cys Gly Cys Cys Cys Thr Cys Cys Ala Ala Thr Cys Gly Gly Gly Thr
                130                 135                 140
Ala Ala Cys Thr Cys Cys Cys Ala Gly Gly Ala Gly Ala Gly Thr Gly
145                 150                 155                 160
Thr Cys Ala Cys Ala Gly Ala Gly Cys Ala Gly Gly Ala Cys Ala Gly
                165                 170                 175
Cys Ala Ala Gly Gly Ala Cys Ala Gly Cys Ala Cys Cys Thr Ala Cys
                180                 185                 190
Ala Gly Cys Cys Thr Cys Ala Gly Cys Ala Gly Cys Ala Cys Cys Cys
                195                 200                 205
Thr Gly Ala Cys Gly Cys Thr Gly Ala Gly Cys Ala Ala Ala Gly Cys
                210                 215                 220
Ala Gly Ala Cys Thr Ala Cys Gly Ala Gly Ala Ala Ala Cys Ala Cys
                225                 230                 235                 240
Ala Ala Ala Gly Thr Cys Thr Ala Cys Gly Cys Cys Thr Gly Cys Gly
                245                 250                 255
```

-continued

```
Ala Ala Gly Thr Cys Ala Cys Cys Cys Ala Thr Cys Ala Gly Gly Gly
            260                 265                 270

Cys Cys Thr Gly Ala Gly Cys Thr Cys Gly Cys Cys Cys Gly Thr Cys
        275                 280                 285

Ala Cys Ala Ala Ala Gly Ala Gly Cys Thr Thr Cys Ala Ala Cys Ala
    290                 295                 300

Gly Gly Gly Gly Ala Gly Ala Gly Thr Gly Thr Thr Ala Ala
305                 310                 315
```

IgA ANTIBODIES AND KITS CAPABLE OF SPECIFICALLY RECOGNIZING RBD PROTEIN

CROSS REFERENCE TO RELATED APPLICATIONS

This application claims priority to International Application No. PCT/CN2020/130496, filed Nov. 20, 2020, which claims priority to Chinese Patent Application No. 202010639269.X, filed on Jul. 6, 2020, and entitled "IGA ANTIBODY SPECIFICALLY RECOGNIZING RBD PROTEIN AND TESTING KIT", wherein the content of said applications are hereby incorporated by reference in their entireties. Also, the entire contents of the ASCII text file entitled "ACL0115US_SEQUENCE_LISTING_2.txt" created on Oct. 27, 2022, having a size of 24 kilobytes, is incorporated herein by reference.

TECHNICAL FIELD

The disclosure relates to the technical field of virus detection, in particular, to an IgA antibody and a kit capable of specifically recognizing RBD protein.

BACKGROUND

The novel coronavirus (SARS-CoV-2, also known as 2019-nCoV or HCoV-19), which belongs to genus beta coronavirus, has particles that are round or oval in shape and with a diameter being 60 nm to 140 nm, significantly differs from SARS in genetic characteristics, and has higher infectivity than SARS. Based on epidemiological investigation, the incubation period of COVID-19 ranges from 1 to 14 days, mostly 3 to 7 days, and the main manifestations of COVID-19 are fever, dry cough, and fatigue. Most severe patients develop dyspnea and/or hypoxemia one week after onset, and critically ill patients may progress rapidly to acute respiratory distress syndrome, septic shock, refractory metabolic acidosis, coagulopathy, multiple organ failure etc. Therefore, how to quickly confirm the diagnosis for suspect cases and how to effectively monitor the progress of the disease will be focus of the treatment of COVID-19 and the battle against the epidemic.

According to the "Diagnosis and Treatment Protocol for Novel coronavirus pneumonia (Trial Version 6)", currently, the method for diagnosis with COVID-19 is to detect a positive nucleic acid of novel coronavirus by using real-time fluorescent RT-PCR or to sequence the viral gene as being highly homologous to known novel coronavirus. However, as the epidemic evolves, the nucleic acid detection reagent has been repeatedly exposed to false-negative problem nowadays, and the positive detection rate ranges from 30% to 50% only, mainly due to the limitation of sampling mode. For the detection of nucleic acid, nasopharyngeal swabs, sputum, blood, and feces from suspected patients is generally collected or RNA fragments are extracted for fluorescent RT-PCR. During sampling, a large number of human cells and bacteria will be blended, resulting in a low abundance of RNA to be tested, which can not be detected by the detection system, and eventually leading to false-negative outcomes. At the same time, sampling methods other than blood sampling will cause sample collection personnel to be exposed to an environment that may contain pathogens, and has a potential risk of infection. The process for preparing a sample requires many steps and a long operation time, as well as a highly skilled inspector.

In the human immune response, IgA antibody, appearing slightly later than IgM antibody and earlier than IgG antibody, is the main early antibody for human against infection and can indicate a recent infection by a positive test. According to the previous research results on SARS and the latest research reports on the novel coronavirus, after the patient is infected with the virus, IgM antibody will be produced in about 3 to 7 days, followed by IgA antibody, and IgG antibody will also rise after 1 week. Clinically, detection of IgM antibody, IgA antibody and IgG antibody can assist in diagnosis, monitoring of the disease and determining the effectiveness of treatment. Detection of IgA in combination with IgM can effectively make up for the possible false positive or false negative outcomes that are given rise by IgM reagents, improve the diagnostic accuracy, and have important clinical value in shortening the window period of post-infection detection.

With a special instrument, the chemiluminescence technology is used for the detection of chemiluminescence intensity mainly based on the principle that the concentration of the analyte in the detection system is in a quantitatively linear relationship with the chemiluminescence intensity of the system under a certain condition, so as to determine the content of the analyte. The chemiluminescence technology has outstanding advantages of high sensitivity, fast reporting speed and a high degree of automation, etc, and has been widely used in the field of medical assay. According to the reaction principle, chemiluminescence technology can be divided into indirect methods, capture methods, competition methods and sandwich methods. Among them, the indirect methods in which an antigen is coated on the surface of a solid phase allows for the rapid enrichment of the antibody to be tested according to the immunological principle of antigen-antibody binding, and for the detection of the content of the antibody to be tested by a suitable secondary antibody.

The novel coronavirus genes encode a variety of structural proteins, the most important one of which is the spike (S) protein (spike glycoprotein). The S protein is probably the earliest antigen recognized by the immune system. The novel coronavirus enters a host cell utilizing the highly glycosylated homotrimeric S protein. The S protein undergoes multiple structural rearrangements to fuse the virus into the membrane of the host cell. This process involves binding the S1 subunit of the virus to a receptor of the host cell, triggering the occurrence of trimeric instability, and one of the three RBDs in the S protein spirals and protrudes upwards, leading to shedding of the S1 subunit and folding of the S2 subunit, thereby enabling the S protein more likely to bind to angiotensin-converting enzyme 2 (ACE2), which is a receptor of the host. The trimer is predominantly in a state that one of the three receptor domains (RBDs) spirals up into a receptor-bindable conformation. Biophysical and structural evidence show that a trimer of the novel coronavirus binds more easily to the ACE2 protein on the cell surface compared with the previous SARS coronavirus. Therefore, RBD protein is the most important protein site for early diagnosis of novel coronavirus. The selection of antigen will directly affect the performance of reagents for detecting an IgA antibody against the novel coronavirus. At the same time, the accuracy and sensitivity for determining IgA antibody will be decreased due to the possible competitive binding of IgM antibody and IgG antibody to the antigen. Therefore, how to solve these problems is the main problem that needs to be overcome in the accurate measurement of IgA antibody against the novel coronavirus.

In addition, the blood containing IgA antibody against novel coronavirus cannot be used as a calibrator material for the detection of IgA antibody against novel coronavirus due to its potential pathogenicity. Therefore, the key to guaranteeing the performance of reagents is to develop an alternative to IgA antibody against novel coronavirus.

SUMMARY OF THE INVENTION

The disclosure relates to an antibody comprising heavy chain complementarity determining regions H-CDR1, H-CDR2, and H-CDR3 having amino acid sequences as set forth in SEQ ID NOs:1~3, respectively, and light chain complementarity determining regions L-CDR1, L-CDR2, and L-CDR3 having amino acid sequences as set forth in SEQ ID NOs:4~6, respectively.

The disclosure further relates to a nucleic acid for encoding the antibody, a vector comprising the nucleic acid, and a host cell comprising the nucleic acid or the vector.

According to yet another aspect of the disclosure, the disclosure further relates to a method for producing said antibody.

The disclosure further relates to use of the antibody as described above as a calibrator of an IgA antibody against the RBD protein of SARS-CoV-2.

According to a further aspect of the disclosure, the disclosure further relates to a kit comprising said antibody.

Compared with the prior art, the disclosure has the following beneficial effects:
  the antibody provided by the disclosure is first used in the detection of IgA antibody against the novel coronavirus, and can specifically bind to the RBD protein of SARS-CoV-2, especially the recombinant RBD protein and its related fragments provided by the disclosure, with high binding affinity.

Automated, high-throughput, and rapid detection of IgA antibody against novel coronavirus pneumonia can be realized by the kit containing the antibody.

DESCRIPTION OF THE DRAWINGS

To illustrate the technical solutions according to the embodiments of the disclosure or in the prior art more clearly, the accompanying drawings for describing the embodiments or the prior art are introduced briefly in the following. Apparently, the accompanying drawings in the following description are only some embodiments of the disclosure, and persons of ordinary skill in the art can derive other drawings from the accompanying drawings without creative efforts.

DETAILED DESCRIPTION OF THE EMBODIMENTS

Reference will now be made in detail to embodiments of the disclosure, one or more examples of which are described below. Each example is provided by way of illustration, instead of limiting the present disclosure. In fact, it will be apparent to those skilled in the art that various modifications and variations can be made to the disclosure without departing from the scope or spirit of the disclosure. For example, features illustrated or described as part of one embodiment can be used in another embodiment to result in a still further embodiment.

Therefore, it is intended that this disclosure covers such modifications and changes as fall within the scope of the appended claims and their equivalents. Other objects, features and aspects of the disclosure are described below or will be apparent from the following detailed description. It should be understood by those of ordinary skill in the art that this discussion is description of exemplary embodiments only, and is not intended to limit the broader aspects of the disclosure.

The disclosure relates to an antibody comprising heavy chain complementarity determining regions H-CDR1, H-CDR2, and H-CDR3 having amino acid sequences as set forth in SEQ ID NOs:1~3, respectively, and light chain complementarity determining regions L-CDR1, L-CDR2, and L-CDR3 having amino acid sequences as set forth in SEQ ID NOs:4~6, respectively.

The antibody can specifically recognize the RBD protein of SARS-CoV-2, especially a recombinant RBD protein and its related fragments (especially undenatured fragments) provided in this application.

The technical term "antibody" used in the disclosure is a protein that binds to a specific antigen, generally referring to all proteins and protein fragments comprising complementarity determining regions (CDR regions), especially a full-length antibody or antibody functional fragments thereof. The term "full-length antibody" includes both polyclonal and monoclonal antibodies, and an antibody may lack at least some of the amino acids that would be present in the full-length chain while still being able to specifically bind to the antigen. Such fragments are biologically active because they bind to the target antigen and can compete with other antigen-binding molecules, including an intact antibody, for binding to a given epitope. In an aspect, such fragments will comprise a single heavy chain and a single light chain, or portions thereof. Such fragments can be produced by nucleic acid recombination, or can be produced by enzymatic or chemical cleavage of antigen-binding molecules including an intact antibody.

In some embodiments, the antibody is a mouse-derived antibody, a human-mouse chimeric antibody, or a humanized antibody.

The term "mouse-derived antibody" used in the disclosure is a monoclonal antibody against RBD protein prepared according to knowledge and skills in the art. During preparation, subjects to be tested are injected with RBD antigen, and hybridomas expressing an antibody having the desired sequence or functional properties are isolated. In a preferred embodiment of the disclosure, the murine-derived antibody or antigen-binding fragment thereof may further comprise a light chain constant region of a murine κ, λ chain or a variant thereof, or further comprise a heavy chain constant region of murine IgG1, IgG2, IgG3, or a variant thereof, preferably an IgA constant region.

The term "chimeric antibody" is an antibody obtained by fusing the variable region of a murine antibody with the constant region of a human antibody, which can reduce the immune response induced by the murine antibody. A chimeric antibody is established by first establishing a hybridoma that secretes a specific murine monoclonal antibody, then cloning a variable region gene from the murine hybridoma cells, cloning a constant region gene of the human antibody as needed, linking the murine variable region gene to the human constant region gene into a chimeric gene, inserting the chimeric gene into an expression vector, and finally expressing the chimeric antibody molecule in a eukaryotic system or a prokaryotic system.

The antibody heavy chain of the chimeric antibody further preferably comprises a human-derived IgA constant region.

The term "humanized antibody", also known as CDR-grafted antibody, refers to an antibody produced by grafting a murine CDR sequence into a variable region framework of a human antibody, i.e., a different type of human germline antibody framework sequence. The heterologous reaction induced by the chimeric antibody due to carrying a large amount of murine protein component can be overcome. Such framework sequences may be available in public DNA databases or published documents that include sequences of germline antibody genes. For example, the germline DNA sequences of human heavy and light chain variable region genes are available in the human germline sequence database "VBase" (www.mrccpe.com.ac.uk/vbase), and in Kabat, E. A. et al, (1991) Sequences of Proteins of Immunological Interest, Fifth Edition. To avoid a decreased activity due to decreased immunogenicity, the variable region framework sequence of the human antibody can be subjected to minimal reverse mutation or back mutation to maintain the activity. The humanized antibody of the present disclosure further includes a humanized antibody in which CDRs are further subjected to affinity maturation by phage display.

In some embodiments, the antibody further comprises heavy chain framework regions H-FR1, H-FR2, H-FR3 and H-FR4 having sequences as set forth in SEQ ID NOs: 7-10, respectively; and/or light chain framework regions L-FR1, L-FR2, L-FR3 and L-FR4 having sequences as set forth in SEQ ID NOs: 11-14, respectively.

In a preferred embodiment, the antibody has a constant region, the constant region of the heavy chain has a sequence selected from IgA, and a species source of the constant region is selected from human.

Optionally, the constant region of the heavy chain has a sequence as set forth in SEQ ID NO: 19;

Optionally, the constant region of the light chain has a sequence as set forth in SEQ ID NO: 20.

In an implementation scenario of the antibody of the disclosure, the antibody is used as a calibrator. It is difficult to obtain IgA antibody against novel coronavirus. The antibody provided by the disclosure has been humanized, and has a structure that is basically the same as that of human endogenous IgA, so it is more accurate when used as a calibrator. Meanwhile, the antibody can be used directly in combination with the anti-human secondary antibody in the kit, which is more convenient and can reduce the systematic error caused by the introduction of additional reagents.

The disclosure further relates to a nucleic acid encoding the antibody as described above.

Generally, the nucleic acid is RNA or DNA, and the nucleic acid molecule can be single-stranded or double-stranded, preferably a double-stranded DNA. A nucleic acid is "operably linked" when it is in a functional relationship with another nucleic acid sequence. For example, a promoter or an enhancer is operably linked to a coding sequence if the promoter or enhancer affects the transcription of the coding sequence. DNA nucleic acid is preferably used when it is ligated into a vector.

Furthermore, since the antibody is a membrane protein, the nucleic acid typically carries a signal peptide sequence.

The disclosure also relates to a vector comprising the nucleic acid as described above.

The disclosure also provides a cell comprising the nucleic acid as described above or the vector as described above.

A suitable host cell or cell line for expressing the antigen binding protein of the disclosure includes mammalian cells such as NSO, Sp2/0, CHO, COS, HEK, fibroblasts and myeloma cells. Human cells can be used, thus allowing molecules to be modified with human glycosylation pattern. Alternatively, other eukaryotic cell lines can be employed. The selection of suitable mammalian host cells, as well as methods for transformation, culture, expansion, screening, and product preparation and purification, are known in the art.

The disclosure further provides a method for producing the antibody as described above, comprising:
  culturing the host cell as described above under a suitable culture condition; and
  recovering the antibody thus produced from a culture medium or from the cultured host cell.

The disclosure further provides a kit comprising the antibody as described above.

In particular, the kit is used to detect RBD protein or an antibody against RBD protein.

In some embodiments, the kit further comprises a recombinant RBD protein of SARS-CoV-2, a solid-phase carrier, a secondary antibody, and a signal substance for labeling the secondary antibody;
  the recombinant RBD protein of SARS-CoV-2 has a signal peptide sequence, an RBD protein sequence as set forth in SEQ ID NO: 15, a transmembrane domain sequence as set forth in SEQ ID NO: 16, and a tag sequence as set forth in SEQ ID NO: 17 in order from N-terminus to C-terminus; preferably, the signal peptide sequence has a sequence as set forth in SEQ ID NO: 18;
  the sequence of RBD protein as set forth in SEQ ID NO: 15 is a conserved sequence of SARS-CoV-2, which is beneficial to improve the positive rate as well as the sensitivity and specificity for detection. The transmembrane domain and the tag peptide are linked to the C-terminus of RBD protein. On the one hand, the transmembrane domain keeps the recombinant protein on the cell membrane, which is conducive to the stability of the protein and facilitates the collection of cells by centrifugation and the enrichment of proteins; on the other hand, the intracellular tag peptide at the C-terminus of RBD protein can be captured by the corresponding tag antibody, eliminating the step of purifying the protein. The signal peptide guides RBD protein to be extracellularly secreted, resulting in post-translational modification, which is conducive to the formation of the correct spatial structure. Therefore, fusion with the transmembrane domain and the C-terminal tag peptide at the C-terminus of the RBD protein is beneficial to the stability of the recombinant protein, and can further improve the sensitivity and specificity for detection in combination with use of a ligand specific for the tag sequence.

The secondary antibody specifically recognizes a human IgA antibody.

In some embodiments, the species source of the secondary antibody is mouse.

In some embodiments, the solid-phase carrier is magnetic beads.

In some embodiments, the recombinant RBD protein of SARS-CoV-2 is coupled to the solid-phase carrier.

In some embodiments, the recombinant RBD protein of SARS-CoV-2 is coupled to the solid-phase carrier in a buffer containing a surfactant Triton from 0.5% to 5% (volume concentration; preferably 1%); and the surfactant Triton is packaged in the kit.

In some embodiments, Triton is one or more selected from Triton X-100, Tween-20, Tween-80, Triton X-405, Triton X-114, Triton X-10, or Triton X-40.

The surfactant can keep the fusion protein in an extended state.

In some embodiments, the signal substance is labeled to the secondary antibody.

In some embodiments, the signal substance includes one or more of acridinium ester, acridine sulfonamide, acridine toluenesulfonamide, acridine p-methylsulfonamide, and acridine trifluoromethanesulfonamide.

In some embodiments, the kit further includes a sample-diluting component and/or a calibrator diluent.

In some embodiments, the sample-diluting component includes one or more of a buffer reagent, BSA, an anti-human IgG antibody, dithiothreitol, cholesterol, trehalose, mannitol, glycine, arginine, glutathione, casein, a surfactant and a preservative.

For testing a sample containing RF interference, the anti-human IgG antibody can coagulate the RF antibody bound to human IgG by adsorbing IgG antibody in the sample, preventing the RF antibody in the sample from binding to the capture antibody through non-specific binding and interfering with the test result, thereby improving the specificity for detection.

The disclosure also relates to the use of the kit as described above in the detection of SARS-CoV-2.

Such use may be for diagnostic or non-diagnostic purposes.

Such use may be used for diagnosis of novel coronavirus pneumonia (COVID-19).

A subject in the above use can refer to patients or animals suspected of carrying SARS-CoV-2, especially mammals, such as bats and civet cats; preferably primates, more preferably humans.

The sample used in the detection of SARS-CoV-2 is preferably upper respiratory tract specimens (such as throat swabs, nasal swabs, etc.), lower respiratory tract specimens (such as respiratory tract aspirates, bronchial lavage fluid, alveolar lavage fluid, deep sputum, etc.), conjunctival swabs from eyes, stool samples, anticoagulation and serum samples, etc. It should try to collect respiratory tract specimens (especially lower respiratory tract specimens) in the early stage of onset of the disease, acute phase serum within 7 days of onset, and convalescent serum from the $3^{rd}$ to $4^{th}$ week after onset of the disease as a clinical sample.

The embodiments of the disclosure will be described in detail below with reference to the examples.

Example 1 Preparation of Recombinant RBD Protein

The following substances were selected:
an RBD protein of the novel coronavirus spike protein having the following amino acid sequence:

(SEQ ID NO: 15)
NITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFT

GCVIAWNSNNLDSKVGGNYNYLYRLFRKSNLKPFERDISTEIYQAGSTPC

NGVEGFNCYFPLQSYGFQPTNGVGYQPYRVVVLSFELLHAPATVCGPKKS

T;

a signal peptide having the following amino acid sequence:

(SEQ ID NO: 18)
MFVFLVLLPLVSSQCV;

a transmembrane domain having the following amino acid sequence:

(SEQ ID NO: 16)
ELWLVLVAVGAGLLLLGLIILLL;

a tag sequence having the following amino acid sequence:

(SEQ ID NO: 17)
WGQGGTHGQWNKPSKP.

The signal peptide, the RBD protein, the transmembrane domain and the tag peptide were connected in order and fused to form an RBD recombinant antigen.

DNA encoding the RBD recombinant protein was obtained by gene synthesis (General Biosystems (Anhui) Co., Ltd.). The DNA of the RBD recombinant antigen had a Hind III site and a Kozak sequence upstream and an EcoR I site downstream. This DNA was digested with the corresponding restriction endonucleases and ligated into a shuttle expression vector pcDNA3.1(+) digested with Hind III and EcoR I enzymes to obtain a recombinant plasmid pcDNA3.1 (+)-RBD.

The recombinant plasmid was transformed into *E. coli* clone strain Top 10, and a single clone was picked, inoculated into 100 mL of LB medium containing 100 μg/ml ampicillin, and cultured at 37° C. and 200 rpm overnight for extraction of the recombinant plasmid. The recombinant plasmid was extracted using an endotoxin-free plasmid extraction kit (TIANGEN BIOTECH (BEIJING) CO., LTD., DP120). 293T cells were plated on a dish and cultured to about 85% confluence for transfection with the recombinant plasmid pcDNA3.1(+)-RBD.

A dish of cells was transfected with 10 μg of plasmid DNA in a mass ratio of plasmid DNA to PEI of 1:5. After the plasmid DNA and PEI were each mixed with 250 μl of PBS, the two mixtures were vortexed and mixed for 1 min. After standing at room temperature for 15 min, the two mixtures were evenly added dropwise into a cell culture dish. After well mixing, the cell culture dish was then placed in an incubator for 48 hours. The transfected cells were scraped off, resuspended in PBS and washed twice, and then a dish of cells was resuspended in 1 ml of a buffer (buffer A) of 10 mM $Na_2HPO_4$/50 mM NaCl/1% Triton X-100, pH 7.4, and placed at 4° C. for extraction for 30 min. The extract was centrifuged at 16,000 g for 15 min, and the supernatant was the extracted recombinant RBD antigen, and stored at −20° C. for later use.

Figure 1:
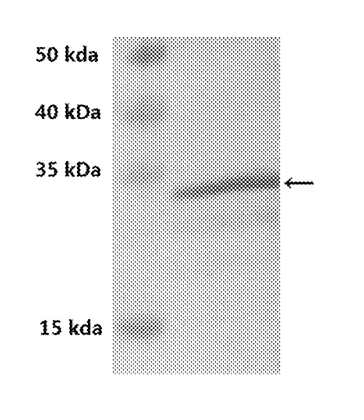
FIG. 1 is an image from Western-blotting (WB) of a transfected cell sample according to an embodiment of the disclosure.

It was confirmed by western blotting assay (WB) that the target protein obtained through the above extraction steps was expressed, and the target protein was detected to be expressed. Because the RBD protein has glycosylation sites, the image from western blotting showed a larger relative molecular weight than the theoretical relative molecular weight. The electrophoresis results are shown in FIG. 1. It has been verified that the protein can effectively bind to IgG antibody, IgM antibody and IgA antibody against novel coronavirus, and can be used in the preparation of reagents for diagnosis of the novel coronavirus in vitro, such as enzyme-linked immunity, colloidal gold, fluorescence immunity, chemiluminescence, etc.

Example 2 Preparation of IgA Antibody

In order to address the inaccessible IgA-positive substances for the novel coronavirus, we modified the structure of the antibody based on the self-produced monoclonal antibody against RBD protein having an S1 subunit, and produced a humanized IgA antibody (C2A-1) that can specifically recognize the RBD protein. The antibody comprises heavy chain complementarity determining regions H-CDR1, H-CDR2, and H-CDR3 having amino acid sequences as set forth in SEQ ID NOs:1~3, respectively, and light chain complementarity determining regions L-CDR1, L-CDR2, and L-CDR3 having amino acid sequences as set forth in SEQ ID NOs:4~6, respectively. The antibody further comprises heavy chain framework regions H-FR1, H-FR2, H-FR3 and H-FR4 having sequences as set forth in SEQ ID NOs: 7-10, respectively; and light chain framework regions L-FR1, L-FR2, L-FR3 and L-FR4 having sequences as set forth in SEQ ID NOs: 11-14, respectively. After testing, the recombinant antibody can effectively recognize the recombinant RBD protein in Example 1, and can be recognized by a commercial mouse anti-human IgA antibody, meeting the requirements of preparing a calibrator for reagents for detecting IgA antibody against novel coronavirus using the recombinant antibody.

Example 3 Preparation of Kit

Meanwhile, the disclosure reveals a method for preparing a chemiluminescence test kit by using the above-mentioned humanized IgA antibody against novel coronavirus and the RBD protein.

In particular, it is necessary to add 1% (from 0.5% to 5%) surfactant Triton X-100 (others such as Tween-20, Tween-80, Triton X-405, Triton X-114, TX-10, TX-40, etc. can be used) into a reaction buffer of magnetic beads and antigen to guarantee that the fusion protein is in an extended state.

In addition, in view of the defects existing in the prior art and the possible oversight in the chemiluminescence detection, we have developed an IgA antibody assay kit against novel coronavirus based on the principle of the indirect immunoassay among the direct chemiluminescence assay. With the corresponding chemiluminescence analyzer, the automated (automatic sampling), high-throughput (100 samples/hour), and rapid detection (reports can be output within 25 minutes) of IgA antibody against novel coronavirus pneumonia can be realized.

The specific components and principle of operation of this kit are as follows:
1. Components of Detection Reagent:
The main components of this kit are a calibrator and a detection reagent, wherein the detection reagent consists of four components:
R1 magnetic bead component: it is composed of magnetic beads coated with RBD protein and having a total concentration of 0.15 mg/ml (from 0.05 mg/ml to 0.5 mg/ml) and a magnetic bead-diluting solution which is a diluent at pH from 5.5 to 8.5 containing 10~100 mM PBS, 0.1~5% BSA, a preservative, a surfactant and other ingredients;
R2 chemiluminescent component: it is composed of mouse anti-human IgA antibody (secondary antibody) labeled with a chemiluminescent label (including but not limited to acridinium ester, acridine sulfonamide, acridine toluenesulfonamide, acridine p-methylsulfonamide, or acridine trifluoromethanesulfonamide) and an acridine diluent, wherein the mouse anti-human IgA antibody is a commercial antibody, and the acridine diluent is a diluent at pH from 5.5 to 8.5 containing 10~100 mM PBS, 0.1-5% BSA, a mouse IgG, a preservative and other components;
R3 sample diluent component: it is composed of a buffer system (10~100 mM PBS), 0.1-5% BSA, a goat anti-human IgG serum from 1% to 10%, 0.1~10 mM dithiothreitol, 1~10 mM cholesterol, 1~10 mM trehalose, 1~200 mM mannitol, 1~50 mM glycine, 1~50 mM arginine, 1~10 mM glutathione, 1~50 mM casein, a surfactant (including but not limited to Tween-20 or Tween-80) from 0.1% to 2%, a preservative (including but not limited to NaN$_3$ or ProClin-300) from 0.1% to 0.5%, etc.;
calibrator (CAL0-CAL3): it is composed of IgA antibody (C2A-1) against novel coronavirus RBD protein purified and prepared in Example 2 and a calibrator diluent, wherein the calibrator diluent is a diluent at pH from 5.5 to 8.5 consisting of 10~100 mM PBS, 0.1-5% BSA, a preservative, a surfactant and other ingredients.

2. Principle of Operation:
This reagent needs to be used in combination with the iFlash-3000 series chemiluminescence analyzer manufactured by us. The cleaning solution, pre-excitation solution, excitation solution and the corresponding cleaning and luminescence reading steps were set by default for the analyzer, and the program for the remaining steps was manually set and completed by the analyzer.
Step 1 dilution of a sample: the program was set to draw 10 ul of the sample into a reaction cup, and the reagent R3 component was added in a dilution ratio of preferably 1:5 (1:2~1:20). After mixing, the mixture was incubated at 37° C. for 5 minutes, so that IgG antibody in the sample was fully adsorbed;
Step 2 addition of magnetic beads: 50 ul of the above reagent R1 component was added into the reaction cup, and incubated at 37° C. for 10 minutes to completely bind IgA antibody in the sample to the fusion protein SARS-COV-2 fAg-5 of the novel coronavirus immobilized on the surface of the magnetic beads. A washing procedure was then performed to wash away the unbound sample;
Step 3 addition of acridine: 100 ul of the above R2 component was added into the cup in which a sufficient reaction was completed, and additionally incubated at 37° C. for 10 minutes, so that the mouse anti-human IgA antibody can fully bind to IgA antibody bound onto the surface of the magnetic bead-antigen complex. A washing procedure is then performed to wash away the unbound antibody;
Step 4 determination of the concentration of the analyte: according to the luminescence program preset by the instrument, the chemiluminescence label bound to the magnetic beads through a series of reactions is excited, and the luminescence value is read from the chemiluminescence analyzer;
Step 5 output of a report: according to the calibration curve and reference interval, the content of IgA antibody against novel coronavirus in the blood or saliva from a patient was reported to assist the clinical diagnosis of the disease.

130 patients were detected by the applicant using the kit provided in the disclosure, and the results are shown in the following table:

|  | positively diagnosed patients | negatively diagnosed patients | total |
|---|---|---|---|
| IgA positive | 58 | 1 | 59 |
| IgA negative | 2 | 69 | 71 |
| total | 60 | 70 | 130 |

It can be seen from the table that this kit leads to a very high positive rate and a very low false positive.

The kit can enable automated (automatic sampling), high-throughput (100 samples/hour), and rapid detection (report will be output within 25 minutes) of IgA antibody against novel coronavirus pneumonia.

The respective technical features mentioned in the same embodiment can be combined arbitrarily as long as they have no collision with each other. For the sake of brevity, all possible combinations of the respective technical features in the above-described embodiments are not described. However, all possible combinations of the respective technical features should be regarded as falling into the scope of the disclosure as long as they have no collision with each other.

The above-mentioned examples are merely illustrative of one or more embodiments of the present disclosure, and the description thereof is more specific and detailed, but should not to be construed as limiting the scope of the disclosure. It should be noted that various variations and modifications may be made by those skilled in the art without departing from the spirit and scope of the disclosure. Therefore, the scope of the disclosure should be subject to the appended claims.

What we claimed is:

1. An antibody, comprising heavy chain complementarity determining regions H-CDR1, H-CDR2, and H-CDR3 having amino acid sequences as set forth in SEQ ID NOs:1~3, respectively, and light chain complementarity determining regions L-CDR1, L-CDR2, and L-CDR3 having amino acid sequences as set forth in SEQ ID NOs:4~6, respectively.

2. The antibody of claim 1, wherein the antibody is a mouse-derived antibody, a human-mouse chimeric antibody, or a humanized antibody.

3. The antibody of claim 1, wherein the antibody has a constant region, the constant region of the heavy chain has a sequence selected from IgA, and a species source of the constant region is selected from human.

4. A nucleic acid encoding the antibody of claim 1.

5. A vector comprising the nucleic acid of claim 4.

6. A host cell comprising the nucleic acid of claim 4.

7. A method for producing an antibody, comprising heavy chain complementarity determining regions H-CDR1, H-CDR2, and H-CDR3 having amino acid sequences as set forth in SEQ ID NOs: 1-3, respectively, and light chain complementarity determining regions L-CDR1, L-CDR2, and L-CDR3 having amino acid sequences as set forth in SEQ ID NOs:4-6, respectively, the method comprising: culturing the host cell of claim 6 under a suitable culture condition; and recovering the antibody thus produced from a culture medium or from the cultured host cell.

8. A kit comprising the antibody of claim 3.

9. The antibody of claim 1, wherein the antibody further comprises heavy chain framework regions H-FR1, H-FR2, H-FR3 and H-FR4 having sequences as set forth in SEQ ID NOs: 7-10, respectively; and/or light chain framework regions L-FR1, L-FR2, L-FR3 and L-FR4 having sequences as set forth in SEQ ID NOs: 11-14, respectively.

10. A host cell comprising the vector of claim 5.

11. The kit of claim 8, further comprising a recombinant (RBD) protein of SARS-CoV-2, a solid-phase carrier, a secondary antibody, and a signal substance for labeling the secondary antibody; the recombinant RBD protein of SARS-CoV-2 has a signal peptide sequence, RBD protein sequence as set forth in SEQ ID NO: 15, a transmembrane domain sequence as set forth in SEQ ID NO: 16, and a tag sequence as set forth in SEQ ID NO: 17 in order from N-terminus to C-terminus, the signal peptide sequence has a sequence as set forth in SEQ ID NO: 18; and the secondary antibody specifically recognizes a human IgA antibody.

12. The kit of claim 11, wherein the solid phase carrier is magnetic beads.

13. The kit of claim 11, wherein the recombinant RBD protein of SARS-CoV-2 is coupled to the solid-phase carrier.

14. The kit of claim 13, wherein the recombinant RBD protein of SARS-CoV-2 is coupled to the solid-phase carrier in a buffer comprising a surfactant at a volume concentration from 0.5% to 5%; wherein the surfactant is packaged in the kit.

15. The kit of claim 11, wherein the signal substance is labeled to the secondary antibody;
the signal substance includes one or more of acridinium ester, acridine sulfonamide, acridine toluenesulfonamide, acridine p-methylsulfonamide, and acridine trifluoromethanesulfonamide.

16. The kit of claim 8, wherein the kit further includes a sample-diluting component.

17. The kit of claim 16, wherein the sample-diluting component includes one or more of a buffer reagent, BSA, an anti-human IgG antibody, dithiothreitol, cholesterol, trehalose, mannitol, glycine, arginine, glutathione, casein, a surfactant and a preservative.

* * * * *